United States Patent
Amano et al.

(10) Patent No.: US 10,141,548 B2
(45) Date of Patent: Nov. 27, 2018

(54) BATTERY PACKAGING MATERIAL, BATTERY, AND METHOD FOR PRODUCING SAME

(71) Applicant: DAI NIPPON PRINTING CO., LTD., Tokyo (JP)

(72) Inventors: Makoto Amano, Tokyo (JP); Rikiya Yamashita, Tokyo (JP); Yoichi Motizuki, Tokyo (JP); Atsuko Takahagi, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 306 days.

(21) Appl. No.: 14/907,640

(22) PCT Filed: Feb. 27, 2015

(86) PCT No.: PCT/JP2015/055940
§ 371 (c)(1),
(2) Date: Jan. 26, 2016

(87) PCT Pub. No.: WO2015/141448
PCT Pub. Date: Sep. 24, 2015

(65) Prior Publication Data
US 2016/0172638 A1  Jun. 16, 2016

(30) Foreign Application Priority Data
Mar. 20, 2014  (JP) ................. 2014-058272

(51) Int. Cl.
*H01M 2/02* (2006.01)
*B32B 15/085* (2006.01)
(Continued)

(52) U.S. Cl.
CPC ......... *H01M 2/0287* (2013.01); *B32B 15/085* (2013.01); *B32B 15/20* (2013.01);
(Continued)

(58) Field of Classification Search
CPC ................. H01M 2/0287; B32B 15/085
USPC ............................................ 429/185
See application file for complete search history.

(56) References Cited

U.S. PATENT DOCUMENTS

| | | | |
|---|---|---|---|
| 2002/0160212 A1 | 10/2002 | Yamashita et al. | |
| 2008/0286635 A1 | 11/2008 | Seino et al. | |

(Continued)

FOREIGN PATENT DOCUMENTS

| JP | 2001-247172 A | 9/2001 |
|---|---|---|
| JP | 2002-050325 A | 2/2002 |

(Continued)

OTHER PUBLICATIONS

Jun. 2, 2015 Search Report issued in International Patent Application No. PCT/JP2015/055940.

(Continued)

*Primary Examiner* — James M Erwin
(74) *Attorney, Agent, or Firm* — Oliff PLC

(57) ABSTRACT

A method for producing a battery packaging material, the method including the steps of: providing a battery packaging material including a laminate in which at least a base material layer, a metal layer, and a sealant layer containing a polyolefin resin are laminated in this order; and confirming that the intensity ratio X=P/Q is in the range of 0.05 to 0.80 where P is a peak intensity P at 1650 $cm^{-1}$ originating from C=O stretching vibration of the amide group of an amide-based lubricant, and Q is a peak intensity Q at 1460 $cm^{-1}$ originating from bending vibration of the group —$CH_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

12 Claims, 1 Drawing Sheet

(51) Int. Cl.
*B32B 15/20* (2006.01)
*B32B 27/32* (2006.01)
*G01N 33/26* (2006.01)
*H01M 2/08* (2006.01)
*G01N 21/3577* (2014.01)
*G01N 21/3563* (2014.01)

(52) U.S. Cl.
CPC ............ *B32B 27/32* (2013.01); *G01N 33/26* (2013.01); *H01M 2/0277* (2013.01); *H01M 2/0285* (2013.01); *H01M 2/08* (2013.01); *B32B 2439/00* (2013.01); *B32B 2457/10* (2013.01); *G01N 21/3563* (2013.01); *G01N 21/3577* (2013.01); *H01M 2002/0297* (2013.01)

(56) References Cited

U.S. PATENT DOCUMENTS

| | | |
|---|---|---|
| 2014/0072864 A1 | 3/2014 | Suzuta et al. |
| 2014/0242450 A1 | 8/2014 | Oono et al. |

FOREIGN PATENT DOCUMENTS

| | | |
|---|---|---|
| JP | 2002-216714 A | 8/2002 |
| JP | 2003-288865 A | 10/2003 |
| JP | 2005-032456 A | 2/2005 |
| JP | 2006-156334 A | 6/2006 |
| JP | 2008-287971 A | 11/2008 |
| JP | 2012-124068 A | 6/2012 |
| JP | 2013-101764 A | 5/2013 |
| JP | 2014-058272 A | 4/2014 |
| JP | 2014-170720 A | 9/2014 |
| WO | 2013/069704 A1 | 5/2013 |

OTHER PUBLICATIONS

Aug. 8, 2017 European Search Report issued in European Application No. 15765213.2.

Mar. 1, 2016 Office Action issued in Japanese Application No. 2015-560447.

Sep. 5, 2018 Office Action issued in Japanese Application No. 2016-131117.

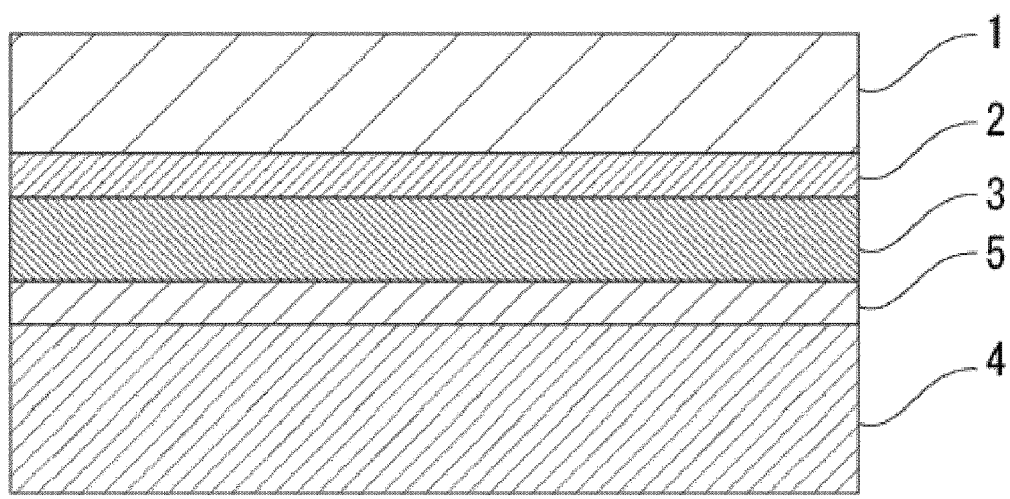

BATTERY PACKAGING MATERIAL, BATTERY, AND METHOD FOR PRODUCING SAME

TECHNICAL FIELD

The present invention relates to a battery packaging material which has high lamination strength and excellent moldability and which is excellent in continuous productivity of batteries. The present invention also relates to a method for measuring the amount of an amide-based lubricant situated on the surface of a sealant layer of a battery packaging material.

BACKGROUND ART

Various types of batteries have been developed heretofore, and in every battery, a packaging material is an essential member for sealing battery elements such as an electrode and an electrolyte. Metallic packaging materials have often been used heretofore as battery packaging materials, but in recent years, batteries have been required to be diversified in shape and to be thinned and lightened with improvement of performance of electric cars, hybrid electric cars, personal computers, cameras, mobile phones and so on. However, metallic battery packaging materials that have often been heretofore used have the disadvantage that it is difficult to keep up with diversification in shape, and there is a limit on weight reduction.

Thus, a film-shaped laminate with a base material layer, an adhesive layer, a metal layer and a sealant layer laminated in this order has been proposed as a battery packaging material which is easily processed into diversified shapes and is capable of achieving thickness reduction and weight reduction (see, for example, Patent Document 1). The film-shaped battery packaging material is formed in such a manner that a battery element can be sealed by heat-welding the peripheral edge by heat sealing with the sealant layers facing each other.

The battery packaging material is molded with a mold at the time of enclosing a battery element, and is provided with a space for storing the battery element. During the molding, the battery packaging material is extended, so that cracks and pinholes are easily generated in a metal layer at a flange portion of the mold. As a method for solving this problem, a method is known in which the surface of a sealant layer of a battery packaging material is coated with an amide-based lubricant, or an amide-based lubricant is blended in a resin for forming a sealant layer, and bled out to the surface to improve the slippage of the sealant layer. When such a method is employed, the battery packaging material is easily drawn in the mold during molding, so that cracks and pinholes in the battery packaging material can be suppressed.

However, there is the problem that if the amount of an amide-based lubricant situated on the surface of the sealant layer is excessively large, the amide-based lubricant is deposited on the mold, and forms a lump to contaminate the mold. If other battery packaging material is molded using the contaminated mold, the lubricant lump deposited on the mold is deposited on the battery packaging material, and involved in heat-sealing of the sealant layer. Consequently, at the time of heat-sealing the sealant layer, the lubricant-deposited portion is unevenly melted, leading to occurrence of a sealing failure. For preventing such a situation, it is necessary to increase the frequency of cleaning for removing the lubricant deposited on the mold, so that the continuous productivity of batteries is deteriorated.

On the other hand, if the amount of the amide-based lubricant situated on the surface of the sealant layer is excessively small, the slippage of a battery packaging material is reduced, so that the moldability of the battery packaging material is deteriorated.

PRIOR ART DOCUMENTS

Patent Documents

Patent Document 1: Japanese Patent Laid-open Publication No. 2008-287971

SUMMARY OF THE INVENTION

Problems to be Solved by the Invention

In a conventional battery packaging material, an amide-based lubricant may be blended in or applied to a sealant layer as described above. As a result of conducting studies by the present inventors, however, it has been found that although the amount of an amide-based lubricant applied to a sealant layer, or the amount of an amide-based lubricant blended in a sealant layer is set to a predetermined amount, the amide-based lubricant may be deposited on a mold during molding of a battery packaging material to deteriorate continuous productivity, or cracks and pinholes may be generated in the battery packaging material. The present inventors have further conducted studies, and resultantly it has been found that in either the case where an amide-based lubricant is blended in or applied to a sealant layer, the amount of the amide-based lubricant situated on the surface of the sealant layer is changed depending on, for example, a storage environment before a battery packaging material is subjected to molding after being produced. Accordingly, the present inventors have conceived that if the amount of an amide-based lubricant situated on the surface of a sealant layer can be measured at the time of subjecting a battery packaging material to molding, it is able to determine beforehand whether or not the battery packaging material has high moldability, and is excellent in continuous productivity of batteries, and thus suitable for production of batteries.

In recent years, the battery packaging material has been required to have a further reduced thickness (e.g. a total thickness of 120 μm or less) for increasing the energy density of a battery, and further reducing the size of the battery. In a very thin battery having such a thickness, pinholes, cracks and the like are easily generated in the battery packaging material if the slippage of a surface of a sealant layer is low during molding, and therefore an amide-based lubricant is often blended for improving moldability.

However, as a result of conducting studies by the present inventors, it has been found that in the case where an adhesive layer is laminated between a metal layer and a sealant layer, pinholes, cracks and the like may be easily generated in a battery packaging material although a predetermined amount of an amide-based lubricant is blended in the sealant layer. The present inventors have further conducted studies for the case of providing the adhesive layer, and resultantly it has also been found that when a predetermined amount of the amide-based lubricant is blended in the sealant layer and the adhesive layer, excellent moldability is exhibited, but lamination strength between the metal layer and the adhesive layer decreases, so that a phenomenon so called delamination may easily occur. The present inventors have further conducted studies, and resultantly it has also been found that the amount of the amide-based lubricant situated on the surface of the sealant layer is excessively large, so that the lubricant may be deposited on the mold, leading to deterioration of continuous productivity of batteries.

Under these circumstances, an object of the present invention is to provide a method for measuring the amount of an amide-based lubricant situated on the surface of a sealant layer of a battery packaging material, and a method for controlling the amount of the amide-based lubricant. Further, an object of the present invention is to provide a battery packaging material which has high lamination strength and excellent moldability and which is excellent in continuous productivity of batteries, and a method for producing the battery packaging material.

Means for Solving the Problem

The present inventors have extensively conducted studies for solving the above-mentioned problems. As a result, it has been found that when in a battery packaging material including a laminate in which at least a base material layer, a metal layer, and a sealant layer containing a polyolefin resin are laminated in this order, the intensity ratio X=P/Q is in the range of 0.05 to 0.80 where P is a peak intensity A at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q, it can be determined that the battery packaging material has high moldability, and is excellent in continuous productivity of batteries, and suitable for production of batteries.

Further, the present inventors have found that a battery packaging material having the following configuration has high lamination strength and excellent moldability, and is also excellent in continuous productivity of batteries.

The battery packaging material includes a laminate in which at least a base material layer, a metal layer, an adhesive layer, and a sealant layer containing a polyolefin resin are laminated in this order. In the battery packaging material, the sealant layer contains an amide-based lubricant, the amount of the amide-based lubricant added to the adhesive layer is 100 ppm or less, and the value Y calculated from the following calculation formula (1) is in the range of 250 to 750.

$$Y=(A\times C+B\times D)/(C+D) \quad (1)$$

A: amount of amide-based lubricant to sealant layer
B: amount of amide-based lubricant to adhesive layer
C: thickness of sealant layer
D: thickness of adhesive layer Further, in the battery packaging material, the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

The present invention has been completed by further conducting studies based on the above-mentioned findings.

That is, the present invention provides an invention of the aspects described below.

Item 1. A battery packaging material including a laminate in which at leak a base material layer, a metal layer, and a sealant layer containing a polyolefin resin are laminated in this order, wherein the intensity ratio X=A/Q is in the range of 0.05 to 0.80 where A is a peak intensity A at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and A/Q is a ratio of the peak intensity A to the peak intensity Q.

Item 2. The battery packaging material according to item 1, wherein the amide-based lubricant is at least one of a fatty acid amide and an aromatic bis-amide.

Item 3. The battery packaging material according to item 1 or 2, wherein an adhesive layer is laminated between the base material layer and the metal layer.

Item 4. The battery packaging material according to any one of items 1 to 3, wherein the amount of the amide-based lubricant to the sealant layer is 500 to 2000 ppm.

Item 5. The battery packaging material according to any one of items 1 to 4, wherein the sealant layer has a thickness of 10 to 30 μm.

Item 6. The battery packaging material according to any one of items 1 to 5, wherein the adhesive layer has a thickness of 10 to 30 μm.

Item 7. The battery packaging material according to any one of items 1 to 6, wherein the laminate has a thickness of 120 μm or less.

Item 8. The battery packaging material according to any one of items 1 to 7, wherein the sealant layer has a crystallinity degree of 30 to 60% as calculated from the spectral intensity ratio of a crystalline portion and a noncrystalline portion of the sealant layer using a Raman spectroscopic method.

Item 9. The battery packaging material according to any one of items 1 to 8, wherein the metal layer is formed of an aluminum foil.

Item 10. A method for measuring the amount of an amide-based lubricant situated on the surface of a sealant layer of a battery packaging material,
the method including the steps of:
providing a battery packaging material including a laminate in which at least a base material layer, a metal layer, and a sealant layer containing a polyolefin resin and an amide-based lubricant are laminated in this order; and
measuring a peak intensity A at 1650 cm$^{-1}$ originating from C=O stretching vibration of the amide group of an amide-based lubricant, and a peak intensity Q at 1460 cm$^{-1}$ originating from bending vibration of the group —CH$_2$— of the polyolefin resin, each from an absorption spectrum obtained by splitting reflected light in irradiation of the surface of the sealant layer with an infrared ray, and calculating an intensity ratio X=P/Q (ratio of the peak intensity P to the peak intensity Q).

Item 11. A method for controlling the amount of an amide-based lubricant situated on the surface of a sealant layer of a battery packaging material,
the method including the steps of:
providing a battery packaging material including a laminate in which at least a base material layer, a metal layer, and a sealant layer containing a polyolefin resin are laminated in this order; and confirming that the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

Item 12. A method for producing a battery packaging material, the method including the steps of:

providing a battery packaging material including a laminate in which at least a base material layer, a metal layer, and a sealant layer containing a polyolefin resin are laminated in this order; and confirming that the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

Item 13. A battery including a battery element which includes at least a positive electrode, a negative electrode and an electrolyte, the battery element being stored in the battery packaging material according to any one of items 1 to 9.

Item 14. A method for producing a battery, the method including the steps of:

providing a battery packaging material including a laminate in which at least a base material layer, a metal layer, and a sealant layer containing a polyolefin resin are laminated in this order;

confirming that the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q; and molding the battery packaging material with the intensity ratio X being in the range of 0.05 to 0.80, and storing in the battery packaging material a battery element including at least a positive electrode, a negative electrode and an electrolyte.

Advantages of the Invention

According to the present invention, there can be provided a battery packaging material which has high lamination strength and excellent moldability and which is excellent in continuous productivity of batteries; a method for producing the battery packaging material; a battery obtained using the battery packaging material; and a method for producing the battery. Further, according to the present invention, there can be provided a method for measuring the amount of an amide-based lubricant situated on the surface of a sealant layer of a battery packaging material, and a method for controlling the amount of the amide-based lubricant.

BRIEF DESCRIPTION OF THE DRAWINGS

FIG. 1 is a drawing showing one example of a cross-sectional structure of a battery packaging material according to the present invention.

EMBODIMENTS OF THE INVENTION

A battery packaging material according to the present invention includes a laminate in which at least a base material layer, a metal layer, an adhesive layer, and a sealant layer containing a polyolefin resin are laminated in this order, wherein the sealant layer contains an amide-based lubricant, the amount of the amide-based lubricant added to the adhesive layer is 100 ppm or less, and the value Y calculated from the following formula (1) is in the range of 250 to 750.

$$Y=(A \times C + B \times D)/(C+D) \qquad (1)$$

A: amount of amide-based lubricant to sealant layer
B: amount of amide-based lubricant to adhesive layer
C: thickness of sealant layer
D: thickness of adhesive layer Further, the battery packaging material according to the present invention has an intensity ratio X=P/Q of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q. Hereinafter, the battery packaging material according to the present invention, a method for producing the battery packaging material, a battery obtained using the battery packaging material, a method for producing the battery, a method for measuring the amount of an amide-based lubricant situated on the surface of the sealant layer of the battery packaging material, and a method for controlling the amount of the amide-based lubricant will be described in detail.

1. Laminated Structure of Battery Packaging Material

The battery packaging material includes a laminate in which at least a base material layer 1, a metal layer 3, an adhesive layer 5 and a sealant layer 4 are laminated in this order as shown in FIG. 1. In the battery packaging material according to the present invention, the base material layer 1 is an outermost layer, and the sealant layer 4 is an innermost layer. That is, at the time of assembling a battery, the sealant layer 4 situated on the periphery of a battery element is heat-sealed with itself to hermetically seal the battery element, so that the battery element is encapsulated.

As shown in FIG. 1, the battery packaging material according to the present invention may be provided with an adhesive agent layer 2 between the base material layer 1 and the metal layer 3 as necessary in order to improve adhesion of these layers. A coating layer may be provided on the base material layer 1 on a side opposite to the metal layer 3 although not illustrated.

2. Compositions of Layers Forming Battery Packaging Material

[Base Material Layer 1]

In the battery packaging material according to the present invention, the base material layer 1 is a layer situated on the outermost layer when the later-described coating layer is not formed. The material that forms the base material layer 1 is not particularly limited as long as it has insulation quality. Examples of the material that forms the base material layer 1 include polyesters, polyamides, epoxy resins, acrylic resins, fluororesins, polyurethanes, silicon resins, phenol resins, polyether imides, polyimides, and mixtures and copolymers thereof.

Specific examples of the polyester include polyethylene terephthalate, polybutylene terephthalate, polyethylene naphthalate, polybutylene naphthalate, polyethylene isophthalate, polycarbonate, copolymerization polyesters with ethylene terephthalate as a main repeating unit, and copolymerization polyesters with a butylene terephthalate as a main repeating unit. Specific examples of the copolymerization polyester including ethylene terephthalate as a main repeating unit include copolymer polyesters that are polymerized with ethylene isophthalate and include ethylene terephthalate as a main repeating unit (hereinafter, abbreviated as follows after polyethylene(terephthalate/isophthalate)), polyethylene(terephthalate/isophthalate), polyethylene(terephthalate/adipate), polyethylene(terephthalate/sodium sulfoisophthalate), polyethylene(terephthalate/sodium isophthalate), polyethylene (terephthalate/phenyl-dicarboxylate) and polyethylene(terephthalate/decane dicarboxylate). Specific examples of the copolymerization polyester including butylene terephthalate as a main repeating unit include copolymer polyesters that are polymerized with butylene isophthalate and include butylene terephthalate as a main repeating unit (hereinafter, abbreviated as follows after polybutylene(terephthalate/isophthalate)), polybutylene(terephthalate/adipate), polybutylene(terephthalate/sebacate), polybutylene(terephthalate/decane dicarboxylate) and polybutylene naphthalate. These polyesters may be used alone, or may be used in combination of two or more thereof. A polyester has the advantage that it is excellent in electrolytic solution resistance, so that whitening etc. due to deposition of an electrolytic solution is hard to occur, and thus the polyester is suitably used as a material for formation of the base material layer 1.

Specific examples of the polyamide include aliphatic polyamides such as nylon 6, nylon 66, nylon 610, nylon 12, nylon 46, and copolymers of nylon 6 and nylon 6,6; hexamethylenediamine-isophthalic acid-terephthalic acid copolymerization polyamides containing a structural unit derived from terephthalic acid and/or isophthalic acid, such as nylon 6I, nylon 6T, nylon 6IT and nylon 6I6T (I denotes isophthalic acid and T denotes terephthalic acid), and polyamides containing aromatics, such as polymethaxylylene adipamide (MXD6); cycloaliphatic polyamides such as polyaminomethyl cyclohexyl adipamide (PACM 6); polyamides copolymerized with a lactam component or an isocyanate component such as 4,4'-diphenylmethane-diisocyanate, and polyester amide copolymers and polyether ester amide copolymers as copolymers of a copolymerization polyamide and a polyester or a polyalkylene ether glycol; and copolymers thereof. These polyamides may be used alone, or may be used in combination of two or more thereof. A stretched polyamide film is excellent in stretchability, can prevent occurrence of whitening due to resin breakage in the base material layer 1 during molding, and is thus suitably used as a material for formation of the base material layer 1.

The base material layer 1 may be formed of a uniaxially or biaxially stretched resin film, or may be formed of an unstretched resin film. Among them, a uniaxially or biaxially stretched resin film, particularly a biaxially stretched resin film has improved heat resistance through orientation and crystallization, and is therefore suitably used as the base material layer 1. The base material layer 1 may be formed by coating the top of the metal layer 3 with the above-mentioned material.

Among them, nylons and polyesters are preferred, and biaxially stretched nylons and biaxially stretched polyesters are further preferred, with biaxially stretched nylons being especially preferred, as resin films for formation of the base material layer 1.

The base material layer 1 can also be laminated with at least one of a resin film and a coating which is made of a different material for improving pinhole resistance, and insulation quality as a package of a battery. Specific examples include a multilayer structure in which a polyester film and a nylon film are laminated, and a multilayer structure in which a biaxially stretched polyester and a biaxially stretched nylon are laminated. When the base material layer 1 is made to have a multilayer structure, the resin films may be bonded with the use of an adhesive, or may be directly laminated without the use of an adhesive. Examples of the method for bonding the resin films without the use of an adhesive include methods in which the resin films are bonded in a heat-melted state, such as a co-extrusion method, a sand lamination method and a thermal lamination method. When the resin films are bonded with the use of an adhesive, the adhesive to be used may be a two-liquid curable adhesive, or may be a one-liquid curable adhesive. Further, the adhesion mechanism of the adhesive is not particularly limited, and may be any one of a chemical reaction type, a solvent volatilization type, a heat melting type, a heat pressing type, an electron beam curing type such as that of UV or EB, and so on. Examples of the component of the adhesive include polyester-based resins, polyether-based resins, polyurethane-based resins, epoxy-based resins, phenol resin-based resins, polyamide-based resins, polyolefin-based resins, polyvinyl acetate-based resins, cellulose-based resins, (meth)acryl-based resins, polyimide-based resins, amino resins, rubbers and silicon-based resins.

The friction of the base material layer 1 may be reduced for improving moldability. When the friction of the base material layer 1 is reduced, the friction coefficient of the surface thereof is not particularly limited, and it is, for example, 1.0 or less. Examples of the method for reducing the friction of the base material layer 1 include matting treatment, formation of a thin film layer of a lubricant, and a combination thereof.

Examples of method of matting treatment include a method in which a matting agent is added to the base material layer 1 beforehand to form irregularities on the surface, a transfer method by heating or pressurization with an embossing roll, and a method in which the surface is mechanically roughened using dry or wet blasting, or a file. Examples of the matting agent include fine particles having a particle size of about 0.5 nm to 5 µm. The material of the matting agent is not particularly limited, and examples thereof include metals, metal oxides, inorganic substances and organic substances. The shape of the matting agent is not particularly limited, and examples thereof include a spherical shape, a fibrous shape, a plate shape, an amorphous shape and a balloon shape. Specific examples of the matting agent include talc, silica, graphite, kaolin, montmorilloide, montmorillonite, synthetic mica, hydrotalcite, silica gel, zeolite, aluminum hydroxide, magnesium hydroxide, zinc oxide, magnesium oxide, aluminum oxide, neodymium oxide, antimony oxide, titanium oxide, cerium oxide, calcium sulfate, barium sulfate, calcium carbonate, calcium silicate, lithium carbonate, calcium benzoate, calcium oxalate, magnesium stearate, alumina, carbon black, carbon nanotubes, high-melting-point nylons, crosslinked acrylics, crosslinked styrenes, crosslinked polyethylenes, benzoguanamine, gold, aluminum, copper and nickel. These matting agents may be used alone, or may be used in combination of two or more thereof. Among these matting agents, silica, barium sulfate and titanium oxide are preferred from the viewpoint of dispersion stability, costs and so on. The surface of the matting agent may be subjected to various kinds of surface treatments such as an insulation treatment and dispersibility enhancing treatment.

The thin film layer of a lubricant can be formed by precipitating a lubricant on the surface of the base material layer 1 by bleeding-out to form a thin layer, or depositing a lubricant on the base material layer 1. The lubricant is not particularly limited, and examples thereof include amide-based lubricants as described later, metal soaps, hydrophilic silicones, acrylics grafted with silicone, epoxies grafted with silicone, polyethers grafted with silicone, polyesters grafted with silicone, block silicone acrylic copolymers, polyglycerol-modified silicones and paraffins. These lubricants may be used alone, or may be used in combination of two or more thereof.

The thickness of the base material layer 1 is, for example, 10 to 50 µm, preferably 15 to 30 µm.

[Coating Layer]

The coating layer to be provided as necessary in the battery packaging material according to the present invention is a layer that is situated on the outer side of the base material layer 1 (outermost layer) when a battery is assembled. In the present invention, the coating layer is formed of, for example, a two-liquid curable resin for the purpose of imparting mainly electrolytic solution resistance, slippage and abrasion resistance to the battery packaging material. The two-liquid curable resin that forms the coating layer is not particularly limited as long as it has electrolytic solution resistance, and examples thereof include two-liquid curable urethane resins, two-liquid curable polyester resins and two-liquid curable epoxy resins. A matting agent may be blended in the coating layer for the purpose of, for example, imparting a design property.

Examples of the matting agent include those shown as an example in the above section of [Base Material Layer 1].

The method for forming the coating layer is not particularly limited, and examples thereof include a method in which a two-liquid curable resin for forming the coating layer is applied to one of the surfaces of the base material layer 1. In the case where a matting agent is blended, the matting agent may be added to and mixed with the two-liquid curable resin, followed by applying the mixture.

Preferably, the coating layer is formed as thinly as possible to exhibit electrolytic solution resistance. The thickness of the coating layer is preferably 5 µm or less, more preferably 3 µm or less. The lower limit of the thickness of the coating layer is normally about 2 µm from the viewpoint of electrolytic solution resistance.

[Adhesive Agent Layer 2]

In the battery packaging material according to the present invention, the adhesive agent layer 2 is a layer provided as necessary for bonding the base material layer 1 and the metal layer 3.

The adhesive agent layer 2 is formed from an adhesive capable of bonding the base material layer 1 and the metal layer 3. The adhesive used for forming the adhesive agent layer 2 may be a two-liquid curable adhesive, or may be a one-liquid curable adhesive. Further, the adhesion mechanism of the adhesive used for forming the adhesive agent layer 2 is not particularly limited, and may be any one of a chemical reaction type, a solvent volatilization type, a heat melting type, a heat pressing type and so on.

Specific examples of the resin component of the adhesive that can be used for forming the adhesive agent layer 2 include polyester-based resins such as polyethylene terephthalate, polybutylene terephthalate, polyethylene naphthalate, polybutylene naphthalate, polyethylene isophthalate, polycarbonate and copolymerized polyester; polyether-based adhesives; polyurethane-based adhesives; epoxy-based resins; phenol resin-based resins; polyamide-based resins such as nylon 6, nylon 66, nylon 12 and copolymerized polyamide; polyolefin-based resins such as polyolefins, acid-modified polyolefins and metal-modified polyolefins; polyvinyl acetate-based resins; cellulose-based adhesives; (meth)acryl-based resins; polyimide-based resins; amino resins such as urea resins and melamine resins; rubbers such as chloroprene rubber, nitrile rubber and styrene-butadiene rubber; silicone-based resins; and ethylene fluoride-propylene copolymers. These adhesive components may be used alone, or may be used in combination of two or more thereof. The combination form of two or more adhesive components is not particularly limited, and examples of the adhesive components include mixed resins of polyamides and acid-modified polyolefins, mixed resins of polyamides and metal-modified polyolefins, mixed resins of polyamides and polyesters, mixed resins of polyesters and acid-modified polyolefins, and mixed resins of polyesters and metal-modified polyolefins. Among them, polyurethane-based two-liquid curable adhesives; and polyamides, polyesters or blend resins of these resins and modified polyolefins are preferred because they are excellent in spreadability, durability and transformation inhibition action under high-humidity conditions, thermal degradation inhibition action during heat-sealing, and so on, and effectively suppress occurrence of delamination by inhibiting a reduction in lamination strength between the base material layer 1 and the metal layer 3.

The adhesive agent layer 2 may be made multilayered with different adhesive components. When the adhesive agent layer 2 is made multilayered with different components, it is preferred that a resin excellent in adhesion with the base material layer 1 is selected as an adhesive component to be disposed on the base material layer 1 side, and an adhesive component excellent in adhesion with the metal layer 3 is selected as an adhesive component to be disposed on the metal layer 3 side for improving the lamination strength between the base material layer 1 and the metal layer 3. When the adhesive agent layer 2 is made multilayered with different adhesive components, specific examples of the preferred adhesive component to be disposed on the metal layer 3 side include acid-modified polyolefins, metal-modified polyolefins, mixed resins of polyesters and acid-modified polyolefins, and resins containing a copolymerization polyester.

The thickness of the adhesive agent layer 2 is, for example, 2 to 50 µm, preferably 3 to 25 µm, more preferably 3 to 15 µm.

[Metal Layer 3]

In the battery packaging material according to the present invention, the metal layer 3 is a layer which is intended to improve the strength of the packaging material, and also functions as a barrier layer for preventing ingress of water vapor, oxygen, light and the like into the battery. Specific examples of the metal that forms the metal layer 3 include metal foils such as those of aluminum, stainless steel and titanium. Among them, aluminum is suitably used. For preventing occurrence of creases and pinholes during production of the packaging material, it is preferred to use soft aluminum, for example annealed aluminum (JIS A8021P-O) or (JIS A8079P-O), for the metal layer 3 in the present invention.

The thickness of metal layer 3 is, for example, 10 to 200 μm, preferably 20 to 100 μm.

Preferably, at least one surface, preferably at least the sealant layer 4-side surface, further preferably both surfaces, of the metal layer 3 is subjected to a chemical conversion treatment for stabilization of bonding, prevention of dissolution and corrosion, and so on. Here, the chemical conversion treatment is a treatment for forming an acid resistance film on the surface of the metal layer 3. Examples of the chemical conversion treatment include a chromic acid chromate treatment using a chromic acid compound such as chromium nitrate, chromium fluoride, chromium sulfate, chromium acetate, chromium oxalate, chromium biphosphate, acetylacetate chromate, chromium chloride or chromium potassium sulfate; a phosphoric acid chromate treatment using a phosphoric acid compound such as sodium phosphate, potassium phosphate, ammonium phosphate or polyphosphoric acid; and a chromate treatment using an aminated phenol polymer formed of repeating units represented by the following general formulae (1) to (4). In the aminated phenol polymer, the repeating units represented by the following general formulae (1) to (4) may be contained alone, or may be contained in combination of two or more thereof.

[Chemical Formula 1]

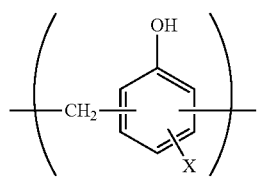

(1)

[Chemical Formula 2]

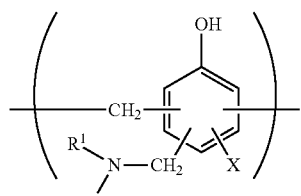

(2)

[Chemical Formula 3]

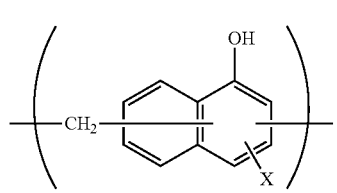

(3)

[Chemical Formula 4]

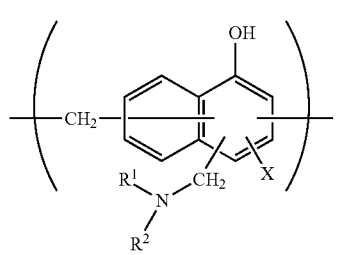

(4)

In the general formulae (1) to (4), X represents a hydrogen atom, a hydroxyl group, an alkyl group, a hydroxyalkyl group, an allyl group or a benzyl group. $R^1$ and $R^2$ are the same or different, and each represent a hydroxyl group, an alkyl group or a hydroxyalkyl group. In the general formulae (1) to (4), examples of the alkyl group represented by X, $R^1$ and $R^2$ include linear or branched alkyl groups having 1 to 4 carbon atoms, such as a methyl group, an ethyl group, an n-propyl group, an isopropyl group, an n-butyl group, an isobutyl group and a tert-butyl group. Examples of the hydroxyalkyl group represented by X, $R^1$ and $R^2$ include linear or branched alkyl groups having 1 to 4 carbon atoms, which is substituted with one hydroxy group, such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group and a 4-hydroxybutyl group. In the general formulae (1) to (4), X is preferably any one of a hydrogen atom, a hydroxyl group, and a hydroxyalkyl group. The number average molecular weight of the aminated phenol polymer formed of repeating units represented by the general formulae (1) to (4) is, for example, about 500 to about 1000000, preferably about 1000 to about 20000.

Examples of the chemical conversion treatment method for imparting corrosion resistance to the metal layer 3 include a method in which the metal layer 3 is coated with a dispersion of fine particles of a metal oxide such as aluminum oxide, titanium oxide, cerium oxide or tin oxide or barium sulfate in phosphoric acid, and annealed at 150° C. or higher to form a corrosion resistance treatment layer on the surface of the metal layer 3. A resin layer with a cationic polymer crosslinked with a crosslinking agent may be formed on the corrosion resistance treatment layer. Here, examples of the cationic polymer include polyethyleneimine, ion polymer complexes formed of a polymer having polyethyleneimine and a carboxylic acid, primary amine-grafted acrylic resins obtained by grafting a primary amine to an acrylic main backbone, polyallylamine or derivatives thereof, and aminophenol. These cationic polymers may be used alone, or may be used in combination of two or more thereof. Examples of the crosslinking agent include compounds having at least one functional group selected from the group consisting of an isocyanate group, a glycidyl group, a carboxyl group and an oxazoline group, and silane coupling agents. These crosslinking agents may be used alone, or may be used in combination of two or more thereof.

These chemical conversion treatments may be performed alone, or may be performed in combination of two or more thereof. The chemical conversion treatments may be performed using one compound alone, or may be performed using two or more compounds in combination. Among them, a chromic acid chromate treatment is preferred, and a chromate treatment using a chromic acid compound, a phosphoric acid compound and the aminated phenol polymer in combination is further preferred.

The amount of the acid resistance film to be formed on the surface of the metal layer 3 in the chemical conversion treatment is not particularly limited, but for example when a chromate treatment is performed using a chromic acid compound, a phosphoric acid compound and the aminated phenol polymer in combination, it is desirable that the chromic acid compound be contained in an amount of about 0.5 mg to about 50 mg, preferably about 1.0 mg to about 40 mg, in terms of chromium, the phosphorus compound be contained in an amount of about 0.5 mg to about 50 mg, preferably about 1.0 mg to about 40 mg, in terms of phosphorus, and the aminated phenol polymer be contained in an amount of about 1 mg to 200 mg, preferably about 5.0 mg to 150 mg, per 1 $m^2$ of the surface of the metal layer 3.

The chemical conversion treatment is performed in the following manner: a solution containing a compound to be used for formation of an acid resistance film is applied to the surface of the metal layer 3 by a bar coating method, a roll coating method, a gravure coating method, an immersion method or the like, and heating is then performed so that the temperature of the metal layer 3 is about 70 to 200° C. The metal layer 3 may be subjected to a degreasing treatment by an alkali immersion method, an electrolytic cleaning method, an acid cleaning method, an electrolytic acid cleaning method or the like before the metal layer 3 is subjected to a chemical conversion treatment. When a degreasing treatment is performed as described above, the chemical conversion treatment of the surface of the metal layer 3 can be further efficiently performed.

[Adhesive Layer 5]

In the battery packaging material according to the present invention, the adhesive layer 5 is a layer provided between the metal layer 3 and the sealant layer 4 as necessary for strongly bonding these layers.

The adhesive layer 5 is formed from a resin capable of bonding the metal layer 3 and the sealant layer 4. The resin to be used for forming the adhesive layer 5 is not particularly limited, but it is preferably a carboxylic acid-modified polyolefin, a carboxylic acid-modified cyclic polyolefin or the like for improving adhesion between the metal layer 3 and the sealant layer 4. Specific examples of the more preferred carboxylic acid-modified polyolefin and carboxylic acid-modified cyclic polyolefin are the same as those shown as an example in the section of [Sealant Layer 4] described later. The resin that forms the adhesive layer 5 and the resin that forms the sealant layer 4 may be the same, or may be different. An olefin-based or styrene-based elastomer component, a rubber component or the like may be blended in the adhesive layer 5 as necessary.

In the case where carboxylic acid-modified polypropylene is used for forming the adhesive layer 5, examples of preferred carboxylic acid-modified polypropylene include those described below:

(1) homo-type polypropylene having a Vicat softening point of 115° C. or higher and a melting point of 150° C. or higher;

(2) ethylene-propylene copolymers having a Vicat softening point of 105° C. or higher and a melting point of 130° C. or higher (random copolymer type); and (3) single or blended products obtained by performing acid modification and polymerization using an unsaturated carboxylic acid having a melting point of 110° C. or higher.

In the present invention, the amount of an amide-based lubricant to be added to the adhesive layer 5 is set to 100 ppm or less. When the upper limit of the amount of the amide-based lubricant to be added to the adhesive layer 5 is set to the above-mentioned value, and the value Y of the later-described calculation formula (1), which is calculated from the amount of the amide-based lubricant added to the adhesive layer 5 and the thickness of the adhesive layer 5, and the amount of the amide-based lubricant added to the later-described sealant layer 4 and the thickness of the sealant layer 4, is set to be in a specific range, high lamination strength between the adhesive layer 5 and the metal layer 3 and excellent moldability can be imparted to the battery packaging material, and continuous productivity of batteries can be improved.

The upper limit of the amount of the amide-based lubricant to be added to the adhesive layer 5 is preferably 50 ppm for imparting further high lamination strength between the adhesive layer 5 and the metal layer 3 and further excellent moldability, and excellent continuous productivity of batteries to the battery packaging material. The lower limit of the amount of the amide-based lubricant to be added to the adhesive layer 5 may be 0 ppm, but is preferably 1 ppm. The amide-based lubricant has a mold release effect, and therefore when a small amount of the amide-based lubricant is contained in a resin, the resin is hardly deposited on a screw and a die during resin extrusion processing, so that degradation of the resin by excessive heating can be prevented, and fish eyes which are caused by carbide etc. can be prevented. Thus, the adhesive layer 5 having a satisfactory external appearance is obtained.

Examples of the amide-based lubricant in the adhesive layer 5 include those that are shown as an example for the sealant layer 4 described later. The amide-based lubricant in the adhesive layer 5 and the amide-based lubricant in the sealant layer 4 may be the same, or may be the different, but preferably the same amide-based lubricant is contained in these layers.

The thickness of the adhesive layer 5 is preferably about 5 to 50 μm, more preferably about 10 to 30 μm, further preferably about 15 to 25 μm.

[Sealant Layer 4]

In the battery packaging material according to the present invention, the sealant layer 4 corresponds to the innermost layer, and during construction of a battery, the sealant layers are heat-welded to each other to hermetically seal the battery element.

The sealant layer 4 is formed of a polyolefin resin. The polyolefin resin is not particularly limited as long as it can be heat-welded, and examples thereof include polyolefins, cyclic polyolefins, carboxylic acid-modified polyolefins and carboxylic acid-modified cyclic polyolefins.

Specific examples of the polyolefin include polyethylene such as low-density polyethylene, medium-density polyethylene, high-density polyethylene and linear low-density polyethylene; polypropylene such as homopolypropylene, block copolymers of polypropylene (e.g. block copolymers of propylene and ethylene) and random copolymers of polypropylene (e.g. random copolymers of propylene and ethylene); terpolymers of ethylene-butene-propylene; and the like. Among these polyolefins, polyethylenes and polypropylenes are preferred.

The cyclic polyolefin is a copolymer of an olefin and a cyclic monomer, and examples of the olefin as a constituent monomer of the cyclic polyolefin include ethylene, propylene, 4-methyl-1-pentene, styrene, butadiene and isoprene. Examples of the cyclic monomer as a constituent monomer of the cyclic polyolefin include cyclic alkenes such as norbornene, specifically cyclic dienes such as cyclopentadiene, dicyclopentadiene, cyclohexadiene and norbornadiene. Among these polyolefins, cyclic alkenes are preferred, and norbornene is further preferred.

The carboxylic acid-modified polyolefin is a polymer with the polyolefin modified by subjecting the polyolefin to block polymerization or graft polymerization with a carboxylic acid. Examples of the carboxylic acid to be used for modification include maleic acid, acrylic acid, itaconic acid, crotonic acid, maleic anhydride and itaconic anhydride.

The carboxylic acid-modified cyclic polyolefin is a polymer obtained by performing copolymerization with an α,β-unsaturated carboxylic acid or an anhydride thereof replacing a part of monomers that form the cyclic polyolefin, or by block-polymerizing or graft-polymerizing an α,β-unsaturated carboxylic acid or an anhydride thereof with the cyclic polyolefin. The cyclic polyolefin to be modified with a carboxylic acid is the same as described above. The carboxylic acid to be used for modification is the same as that used for modification of the acid-modified cycloolefin copolymer.

Among these resin components, carboxylic acid-modified polyolefins are preferred, and carboxylic acid-modified polypropylene is further preferred.

The sealant layer 4 may be formed from one resin component alone, or may be formed from a blend polymer obtained by combining two or more resin components. An olefin-based or styrene-based elastomer component, a rubber component or the like may be blended in the sealant layer 4 as necessary. Further, the sealant layer 4 may be formed of only one layer, but may be formed of two or more layers with the same resin component or different resin components.

The sealant layer 4 contains an amide-based lubricant. In the present invention, the amount of the amide-based lubricant to be added to the adhesive layer 5 is set to 100 ppm or less, and the value Y calculated from the following calculation formula (1) is in the range of 250 to 750 as described above.

$$Y = (A \times C + B \times D)/(C+D) \quad (1)$$

A: amount of amide-based lubricant to sealant layer
B: amount of amide-based lubricant to adhesive layer
C: thickness of sealant layer
D: thickness of adhesive layer As described above, as a result of conducting studies by the present inventors, it has been found that in a battery packaging material with an adhesive layer laminated between a metal layer and a sealant layer, the moldability of the battery packaging material is deteriorated, so pinholes, cracks and the like may be easily generated although the amount of an amide-based lubricant to be added to the sealant layer is set to a conventionally known predetermined amount (e.g. about 100 to 3000 ppm). It has also been found that when the predetermined amount of the amide-based lubricant is added to the sealant layer and the adhesive layer, excellent moldability is exhibited, but lamination strength between the metal layer and the adhesive layer decreases, so that a phenomenon so called delamination may easily occur. Further, a phenomenon has also been found in which the amount of the amide-based lubricant situated on the surface of the sealant layer is excessively large, so that the amide-based lubricant is deposited on a mold during molding, leading to deterioration of continuous productivity of batteries. It has also been found that these phenomena occur although the thickness of each of the adhesive layer and the sealant layer is set to a thickness that has been heretofore considered appropriate.

Under these circumstances, the present inventors have conducted studies, and resultantly, found that when in a battery packaging material with an adhesive layer laminated between a metal layer and a sealant layer, the value Y calculated from the above calculation formula (1) representing a relationship between the thickness of each of the adhesive layer and the sealant layer and the amount of an amide-based lubricant added to each of these layer (concentration of amide-based lubricant) is set so as to fall within the above-mentioned specific range, the battery packaging material has high lamination strength and excellent moldability, and is excellent in continuous productivity of batteries. The reason why when the value Y calculated from the above calculation formula (1) falls within the above-mentioned specific range, these excellent effects are exhibited may be considered as follows. That is, when an amide-based lubricant is added to the sealant layer, the amide-based lubricant also moves between the sealant layer and the adhesive layer if the adhesive layer exists between the sealant layer and the metal layer. In the sealant layer and the adhesive layer, the amount of the amide-based lubricant that can be contained in the layer increases as the thickness becomes larger. Therefore, it can be said that when the amount of the amide-based lubricant to be added to, for example, the sealant layer is the same, the amide-based lubricant also easily moves to the adhesive layer side if the adhesive layer has a large thickness and a low amide-based lubricant concentration. It can be said that conversely, if the adhesive layer has a small thickness and a high amide-based lubricant concentration, the lubricant is hard to move to the adhesive layer side. If the amide-based lubricant concentration of the sealant layer decreases, moldability is deteriorated, and if the amide-based lubricant concentration of the sealant layer increases, the amount of the amide-based lubricant that is bled out increases, leading to deterioration of continuous productivity of batteries. It is considered that if the amide-based lubricant concentration of the adhesive layer increases, adhesion between the metal layer and the adhesive layer easily decreases. Therefore, it is considered that as a result of setting the relational formula (calculation formula (1)) between the thickness of each of the adhesive layer and the sealant layer and the amount of the amide-based lubricant, the concentration of the amide-based lubricant contained in each of the adhesive layer and the sealant layer falls within an appropriate range, so that the battery packaging material has high lamination strength and excellent moldability, and is excellent in continuous productivity of batteries.

The value Y calculated from the calculation formula (1) is more preferably about 300 to 700, further preferably about 400 to 600 for imparting further high lamination strength between the adhesive layer 5 and the metal layer 3 and excellent moldability, and excellent continuous productivity to the battery packaging material.

The amount of the amide-based lubricant to be added to the sealant layer 4 is not particularly limited as long as the value Y falls within the above-mentioned specific range, but it is preferably about 500 to 2000 ppm, more preferably about 700 to 1500 ppm. If the added amount of the amide-based lubricant is less than 500 ppm, the amount of the amide-based lubricant bled out to the surface of the sealant layer in the initial stage may be insufficient, leading to deterioration of moldability. On the other hand, if the amount of the amide-based lubricant is more than 2000 ppm, the amide-based lubricant that is bled out excessively in the initial stage may contaminate the production line, leading to deterioration of continuous productivity of batteries. In the present invention, the amount of the amide-based lubricant contained in the sealant layer 4 is the total amount of the lubricant situated on the inside of the sealant layer 4 and the lubricant situated on the surface of the sealant layer 4.

In the battery packaging material according to the present invention, the amide-based lubricant exists at the surface of the sealant layer 4. As a method for causing the amide-based lubricant to exist at the surface of the sealant layer 4, for example, a method can be employed in which the surface of the sealant layer 4 of the battery packaging material is coated with the amide-based lubricant, or the amide-based lubricant is blended in a polyolefin resin for forming the sealant layer 4, and bled out to the surface.

The amide-based lubricant is not particularly limited as long as it has an amide group, and fatty acid amides and aromatic bis-amides are preferred. The amide-based lubricants may be used alone, or may be used in combination of two or more thereof.

Examples of the fatty acid amide include saturated fatty acid amides, unsaturated fatty acid amides, substituted amides, methylol amides, saturated fatty acid bis-amides and unsaturated fatty acid bis-amides. Specific examples of the saturated fatty acid amide include lauric acid amides, palmitic acid amides, stearic acid amides, behenic acid amides and hydroxystearic acid amides. Specific examples of the unsaturated fatty acid amide include oleic acid amides and erucic acid amides. Specific examples of the substituted amide include N-oleylpalmitic acid amides, N-stearylstearic acid amides, N-stearyloleic acid amides, N-oleylstearic acid amides and N-stearylerucic acid amides. Specific examples of the methylol amide include methylolstearic acid amides. Specific examples of the saturated fatty acid bis-amide include methylene-bis-stearic acid amides, ethylene-bis-capric acid amides, ethylene-bis-lauric acid amides, ethylene-bis-stearic acid amides, ethylene-bis-hydroxystearic acid amides, ethylene-bis-behenic acid amides, hexamethylene-bis-stearic acid amides, hexamethylene-bis-behenic acid amides, hexamethylene-hydroxystearic acid amides, N,N'-distearyladipic acid amides and N,N'-distearylsebacic acid amides. Specific examples of the unsaturated fatty acid bis-amide include ethylene-bis-oleic acid amides, ethylene-bis-erucic acid amides, hexamethylene-bis-oleic acid amides, N,N'-dioleyladipic acid amides and N,N'-dioleylsebacic acid amides. Specific examples of the fatty acid ester amide include stearamide ethyl stearates. Specific examples of the aromatic bis-amide include m-xylylene-bis-stearic acid amides, m-xylylene-bis-hydroxystearic acid amides and N,N'-distearylisophthalic acid amides. Among them, fatty acid amides are preferred, and erucic acid amides are more preferred.

The battery packaging material according to the present invention has an intensity ratio X=P/Q of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer 4 with an infrared ray, and P/Q is a ratio of the peak intensity P to the peak intensity Q. Since the battery packaging material according to the present invention has an intensity ratio X in the above-mentioned specific range, it has high moldability, and is excellent in continuous productivity of batteries. In the present invention, the intensity ratio X=P/Q may be in the range of 0.05 to 0.80, but the intensity ratio X=P/Q is more preferably 0.20 to 0.60.

The intensity ratio X in the present invention is a value determined in the following manner: the battery packaging material is cut to a square of 100 mm×100 mm to prepare a sample, and the surface of the sealant layer of this sample is subjected to infrared absorption spectrum measurement in infrared spectroscopy under an environment at a temperature of 25° C. and a relative humidity of 50% using the ATR mode of Nicolet iS10 FT-IR manufactured by Thermo Fisher Scientific, Inc.

In a conventional battery packaging material, an amide-based lubricant is blended in or applied to a sealant layer as described above. However, it has been found that although the amount of an amide-based lubricant applied to a sealant layer, or the amount of an amide-based lubricant blended in a sealant layer is set to a predetermined amount, the amide-based lubricant may be deposited on a mold during molding of a battery packaging material to deteriorate continuous productivity, or cracks and pinholes may be generated in the battery packaging material. It has been found that this is because in either the case where an amide-based lubricant is blended in or applied to a sealant layer, the amount of the amide-based lubricant situated on the surface of the sealant layer is considerably changed depending on an environment before the battery packaging material is subjected to molding after being produced, such as a storage or transportation environment before the battery packaging material is subjected to molding after being produced, particularly depending on a temperature change. Accordingly, for example, although a constant amount of the amide-based lubricant is used during production of the battery packaging material, the amount of the amide-based lubricant situated on the surface during molding is considerably changed depending on a storage environment etc., so that the amide-based lubricant may be deposited on a mold, leading to deterioration of continuous productivity, or cracks and pinholes may be generated in the battery packaging material. When an environment before the battery packaging material is subjected to molding after being produced, such as a storage or transportation environment before the battery packaging material is subjected to molding after being produced, particularly a temperature change is appropriately controlled, it is possible to suppress a change in amount of the amide-based lubricant after production and before molding of the battery packaging material, but practically, it may be unable to appropriately control the storage and transportation environments, and thus a problem in moldability or continuous productivity may occur only when the battery packaging material is subjected to molding.

On the other hand, the battery packaging material according to the present invention is suitable for production of batteries because the amount of the amide-based lubricant situated on the surface of the sealant layer 4 is set to a value appropriate to moldability and continuous productivity by the above-mentioned infrared absorption spectrum measurement.

3. Method for Producing Battery Packaging Material

While the method for producing a battery packaging material according to the present invention is not particularly limited as long as a laminate including layers each having a predetermined composition is obtained, and examples thereof include a method including the steps of:

providing a battery packaging material including a laminate in which at least a base material layer, a metal layer, and a sealant layer containing a polyolefin resin are laminated in this order; and confirming that the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

In the method for producing a battery packaging material according to the present invention, the above-mentioned adhesive agent layer 2 and adhesive layer 5 may be each laminated on the battery packaging material as necessary. Specific examples of the method for producing a battery packaging material according to the present invention include the following method.

First, a laminate in which the base material layer 1, the adhesive agent layer 2 and the metal layer 3 are laminated in this order (hereinafter, the laminate may be described as a "laminate A") is formed. Specifically, the laminate A can be formed by a dry lamination method in which an adhesive to be used for formation of the adhesive agent layer 2 is applied onto the base material layer 1 or the metal layer 3, the surface of which is subjected to a chemical conversion treatment as necessary, using a coating method such as an extrusion method, a gravure coating method or a roll coating method, and dried, the metal layer 3 or the base material layer 1 is then laminated, and the adhesive agent layer 2 is cured.

Then, the sealant layer 4 is laminated on the metal layer 3 of the laminate A. When the sealant layer 4 is laminated directly on the metal layer 3, a resin component that forms the sealant layer 4 may be applied onto the metal layer 3 of the laminate A by a method such as a gravure coating method or a roll coating method. When the adhesive layer 5 is provided between the metal layer 3 and the sealant layer 4, mention is made of, for example, (1) a method in which the adhesive layer 5 and the sealant layer 4 are co-extruded to be laminated on the metal layer 3 of the laminate A (co-extrusion lamination method); (2) a method in which the adhesive layer 5 and the sealant layer 4 are laminated to form a laminate separately, and the laminate is laminated on the metal layer 3 of the laminate A by a thermal lamination method; (3) a method in which an adhesive for formation of the adhesive layer 5 is laminated on the metal layer 3 of the laminate A by an extrusion method or a method in which the adhesive is applied by solution coating, dried at a high temperature and baked, and the sealant layer 4 formed in a sheet shape beforehand is laminated on the adhesive layer 5 by a thermal lamination method; and (4) a method in which the melted adhesive layer 5 is poured between the metal layer 3 of the laminate A and the sealant layer 4 formed in a sheet shape beforehand, and simultaneously the laminate A and the sealant layer 4 are bonded together with the adhesive layer 5 interposed therebetween (sandwich lamination). The laminate may be further subjected to a heating treatment such as that of heat roll contact type, hot air type or near- or far-infrared ray type, for enhancing the adhesion of the adhesive agent layer 2 and the adhesive layer 5 provided as necessary. As conditions for such a heating treatment, for example, the temperature is 150 to 250° C., and the time is 1 to 5 minutes.

In the battery packaging material according to the present invention, the layers that form the laminate may be subjected to a surface activation treatment such as a corona treatment, a blast treatment, an oxidation treatment or an ozone treatment as necessary for improving or stabilizing film formability, lamination processing and final product secondary processing (pouching and embossing molding) suitability, and the like.

In the method for producing a battery packaging material according to the present invention, a battery packaging material of the present invention, which has high moldability and which is excellent in continuous productivity of batteries can be produced by carrying out the step of confirming that the intensity ratio X=P/Q is in the range of 0.05 to 0.80 using the methods for measurement and calculation of the intensity ratio X=P/Q by infrared absorption spectrum measurement after providing the battery packaging material in which the layers are laminated as described above.

4. Method for Measuring Amount of Amide-Based Lubricant Situated on Surface of Sealant Layer of Battery Packaging Material The method for measuring the amount of an amide-based lubricant situated on the surface of a sealant layer 4 of a battery packaging material according to the present invention includes the following steps of:

providing a battery packaging material including a laminate in which at least a base material layer, a metal layer, and a sealant layer containing a polyolefin resin and an amide-based lubricant are laminated in this order; and measuring a peak intensity P at 1650 cm$^{-1}$ originating from C=O stretching vibration of the amide group of the amide-based lubricant and a peak intensity Q at 1460 cm$^{-1}$ originating from bending vibration of the group —CH$_2$— of the polyolefin resin, each from an absorption spectrum obtained by splitting reflected light in irradiation of the surface of the sealant layer with an infrared ray, and calculating an intensity ratio X=P/Q of the peak intensity P to the peak intensity Q.

The laminated structure of the battery packaging material for which the amount of the amide-based lubricant situated on the surface of the sealant layer is measured, and the compositions of the layers are similar to those described above. In the measurement method according to the present invention, the above-mentioned adhesive agent layer 2 and adhesive layer 5 may be each laminated on the battery packaging material as necessary. The methods for measurement and calculation of the intensity ratio X=P/Q by infrared absorption spectrum measurement are similar to those described above.

When the method for measuring the amount of the amide-based lubricant situated on the surface of the sealant layer of the battery packaging material according to the present invention is carried out, for example, immediately before a battery is produced, whether or not the battery packaging material has high moldability, and is excellent in continuous productivity of batteries, and thus suitable for production of batteries can be determined in advance. That is, a battery packaging material for which it can be confirmed by the measurement method that the intensity ratio X=P/Q is in the range of 0.05 to 0.80 can be judged as a battery packaging material suitable for production of batteries, molded, and provided for production of a battery. A battery packaging material for which it is confirmed that the X=P/Q falls out of the range of 0.05 to 0.80 can be judged as a battery packaging material unsuitable for production of batteries, and prevented from being applied to production of a battery.

5. Method for Controlling Amount of Amide-Based Lubricant Situated on Surface of Sealant Layer of Battery Packaging Material The method for controlling the amount of an amide-based lubricant situated on the surface of a sealant layer 4 of a battery packaging material according to the present invention includes the following steps of:

providing a battery packaging material including a laminate in which at least a base material layer, a metal layer, and a sealant layer containing a polyolefin resin and an amide-based lubricant are laminated in this order; and confirming that the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

The laminated structure of the battery packaging material for which the amount of the amide-based lubricant situated on the surface of the sealant layer is controlled, and the compositions of the layers are similar to those described above. The methods for measurement and calculation of the intensity ratio X=P/Q by infrared absorption spectrum measurement are similar to those described above.

When the method for controlling the amount of the amide-based lubricant situated on the surface of the sealant layer of the battery packaging material according to the present invention is carried out immediately before a battery is produced, whether or not the battery packaging material has high moldability, and is excellent in continuous productivity of batteries, and thus suitable for production of batteries can be determined in advance. That is, a battery packaging material for which it can be confirmed that the intensity ratio X=P/Q is in the range of 0.05 to 0.80 can be judged as a battery packaging material suitable for production of batteries, molded, and provided for production of a battery.

6. Use of Battery Packaging Material

The battery packaging material according to the present invention is used as a packaging material for hermetically sealing and storing battery elements such as a positive electrode, a negative electrode and an electrolyte.

Specifically, a battery element including at least a positive electrode, a negative electrode and an electrolyte is covered with the battery packaging material according to the present invention such that a flange portion (region where sealant layers are in contact with each other) can be formed on the periphery of the battery element while a metal terminal connected to each of the positive electrode and the negative electrode protrudes to outside, and sealant layers at the flange portion are heat-sealed with each other, thereby providing a battery using a battery packaging material. When the battery element is stored using the battery packaging material according to the present invention, the battery packaging material according to the present invention is used such that the sealant portion is on the inner side (surface in contact with the battery element).

The battery according to the present invention can be produced by a production method including the steps of:

providing a battery packaging material including a laminate in which at least a base material layer, a metal layer, and a sealant layer containing a polyolefin resin are laminated in this order; and confirming that the intensity ratio X=P/Q is in the range of 0.05 to 0.80 where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin, each of which is measured from an absorption spectrum obtained by splitting reflected light in irradiation of the surface of the sealant layer with an infrared ray, and P/Q is a ratio of the peak intensity P to the peak intensity Q;

molding a battery packaging material with the intensity ratio X being in the range of 0.05 to 0.80, and storing therein a battery element including at least a positive electrode, a negative electrode and an electrolyte; and confirming that the intensity ratio X=P/Q is in the range of 0.05 to 0.80 before molding the battery packaging material in the process for producing the battery according to the present invention.

Since the method for producing a battery includes the above-mentioned steps, the battery packaging material storing the battery element can be provided for production of a battery after being confirmed to be suitable for production of batteries. In the method for producing a battery according to the present invention, the above-mentioned adhesive agent layer 2 and adhesive layer 5 may also be each laminated on the battery packaging material as necessary.

The battery packaging material according to the present invention may be used for either a primary battery or a secondary battery, but is preferably used for a secondary battery. The type of secondary battery to which the battery packaging material according to the present invention is applied is not particularly limited, and examples thereof include lithium ion batteries, lithium ion polymer batteries, lead storage batteries, nickel-hydrogen storage batteries, nickel-cadmium storage batteries, nickel-iron storage batteries, nickel-zinc storage batteries, silver oxide-zinc storage batteries, metal-air batteries, polyvalent cation batteries, condensers and capacitors. Among these secondary batteries, preferred subjects to which the battery packaging material according to the present invention is applied include lithium ion batteries and lithium ion polymer batteries.

EXAMPLES

The present invention will be described in detail below by showing examples and comparative examples. It is to be noted that the present invention is not limited to examples.

Examples 1 to 7 and Comparative Examples 1 to 6

<Production of Battery Packaging Material>

Both surfaces of an aluminum foil (thickness: 40 µm) as a metal layer were subjected to a chemical conversion treatment, and a resin (thickness: 25 µm) as described in Table 1 was bonded to one of the chemical conversion-treated surfaces as a base material layer with a polyester-based adhesive interposed therebetween by a dry lamination method in such a manner that the thickness of an adhesive agent layer was about 3 µm. Next, an adhesive layer (thickness: 23 µm) formed of carboxylic acid-modified polypropylene and a sealant layer (thickness: 23 µm) formed of a random copolymer of polypropylene with an amide-based lubricant blended therein so as to achieve a content as described in Table 1 were melt-coextruded to the other chemical conversion-treated surface to obtain a laminate including a base material layer, an adhesive agent layer, an aluminum foil, an adhesive layer and a sealant layer. Each battery packaging material was produced at a temperature of 25° C. The chemical conversion treatment was performed in the following manner: an aqueous solution including a phenol resin, a chromium fluoride compound and phosphoric acid was applied as a treatment liquid using a roll coating method, and baked under the condition of a film temperature of 180° C. or higher. The applied amount of chromium was 10 mg/m$^2$ (dry mass).

(Storage Environment)

The battery packaging material of each of Examples 1 to 7 and Comparative Examples 1 to 6 was left standing at a temperature of 25° C. and a relative humidity of 50% for 7 days, followed by evaluating moldability and continuous productivity as described below. The battery packaging material of Comparative Example 5 was left standing at a temperature of 40° C. and a relative humidity of 50% for 7 days, and the battery packaging material in Comparative Example 6 was left standing at a temperature of 50° C. and a relative humidity of 50% for 7 days, followed by performing infrared (IR) absorption spectrum measurement and evaluating moldability and continuous productivity as described below.

(Infrared Absorption Spectrum Measurement in Infrared Spectroscopy)

Each battery packaging material obtained as described above was cut to a square of 100 mm×100 mm to prepare a sample. The surface of the sealant layer of this sample was subjected to infrared absorption spectrum measurement under an environment at a temperature of 25° C. and a relative humidity of 50% using the ATR mode of Nicolet iS10 FT-IR manufactured by Thermo Fisher Scientific, Inc. A peak intensity P at 1650 cm$^{-1}$ originating from C=O stretching vibration of the amide group and a peak intensity Q at 1460 cm$^{-1}$ originating from bending vibration of the group —CH$_2$— of a polyolefin resin were each measured from the obtained absorption spectrum, and an intensity ratio X=P/Q of the peak intensity P to the peak intensity Q was calculated. The results are shown in Table 1.

(Evaluation of Moldability)

Each battery packaging material obtained as described above was cut to a rectangle of 80 mm×120 mm to prepare a sample. Using a mold (female mold) having an opening size (rectangle) of 30 mm×50 mm and a corresponding mold (male mold), the sample was cold-molded while the molding depth was changed by units of 0.5 mm from the molding depth of 0.5 mm under a pressing force of 0.4 MPa. This procedure was carried out for 10 samples at each depth. For the sample after the cold molding, the deepest of depths at which none of the 10 samples had creases, and pinholes and cracks in the aluminum foil was defined as the limit molding depth of the sample. From the limit depth, the moldability of the battery packaging material was evaluated in accordance with the following criteria. The results are shown in Table 1.

A: the limit molding depth is 6.0 mm or more.
B: the limit molding depth is 4.0 mm to 5.5 mm.
C: the limit molding depth is 3.5 mm or less.

(Evaluation of Continuous Productivity of Batteries)

The corner portion of the mold after the evaluation of moldability performed as described above was visually observed. A sample was rated as having low continuous moldability (C) when the mold was whitened with the lubricant transferred thereto, and a sample was rated as having high continuous moldability (A) when the mold was not whitened. The results are shown in Table 1.

TABLE 1

| | Intensity ratio X | Calculated value Y | Amide-based lubricant/content | Storage temperature (° C.) | Base material layer | Metal Layer | Adhesive layer/ sealant layer | Moldability | Continuous productivity |
|---|---|---|---|---|---|---|---|---|---|
| Example 1 | 0.80 | 600 | Erucic acid amide 1200 ppm | 25 | Nylon | Aluminum alloy | Acid-modified PP/PP | A | A |
| Example 2 | 0.63 | 550 | Erucic acid amide 1100 ppm | 25 | PET/nylon | Aluminum alloy | Acid-modified PP/PP | A | A |
| Example 3 | 0.49 | 500 | Behenic acid amide 1000 ppm | 25 | Nylon | Aluminum alloy | Acid-modified PP/PP | A | A |
| Example 4 | 0.51 | 500 | Erucic acid amide 1000 ppm | 25 | Nylon | Aluminum alloy | Acid-modified PE/PE | A | A |
| Example 5 | 0.37 | 450 | Erucic acid amide 900 ppm | 25 | PBT | Aluminum alloy | Acid-modified PP/PP | A | A |
| Example 6 | 0.19 | 400 | Erucic acid amide 800 ppm | 25 | PET | Stainless steel | Acid-modified PP/PP | A | A |
| Example 7 | 0.05 | 350 | Erucic acid amide 700 ppm | 25 | Nylon | Aluminum alloy | Acid-modified PP/PP | A | A |
| Comparative Example 1 | 0.97 | 700 | Erucic acid amide 1400 ppm | 25 | Nylon | Aluminum alloy | Acid-modified PP/PP | A | C |
| Comparative Example 2 | 0.85 | 650 | Erucic acid amide 1300 ppm | 25 | PET/nylon | Aluminum alloy | Acid-modified PP/PP | A | C |
| Comparative Example 3 | 0.03 | 300 | Erucic acid amide 600 ppm | 25 | Nylon | Aluminum alloy | Acid-modified PP/PP | B | A |
| Comparative Example 4 | 0.02 | 250 | Erucic acid amide 500 ppm | 25 | Nylon | Aluminum alloy | Acid-modified PP/PP | C | A |
| Comparative Example 5 | 0.03 | 350 | Erucic acid amide 700 ppm | 40 | Nylon | Aluminum alloy | Acid-modified PP/PP | B | A |
| Comparative Example 6 | 0.01 | 350 | Erucic acid amide 700 ppm | 50 | Nylon | Aluminum alloy | Acid-modified PP/PP | C | A |

The notes in Table 1 are shown below.
PET: polyethylene terephthalate.
PBT: polybutylene terephthalate.
PP: polypropylene (random PP manufactured by Prime Polymer Co., Ltd.).
PE: polyethylene (high.density polyethylene (HDPE) manufactured by Prime Polymer Co., Ltd.). In PET/nylon, PET (12 μm) and nylon (15 μm) are laminated from the outer side of the battery packaging material (on a side opposite to the metal layer).

As is evident from the results shown in Table 1, the battery packaging materials of Examples 1 to 7 where the intensity ratio X=P/Q calculated in infrared spectroscopy is in the range of 0.05 to 0.80 has high moldability and is excellent in continuous productivity. On the other hand, in each of the battery packaging materials of Comparative Examples 1 and 2 where the intensity ratio X=P/Q calculated in infrared spectroscopy was larger than 0.80, the mold was whitened with the lubricant deposited thereon, and continuous productivity of batteries was low. The battery packaging materials of Comparative Examples 3 to 6 where the intensity ratio X=P/Q calculated in infrared spectroscopy was smaller than 0.05 had low moldability. In Comparative Examples 5 and 6, the use amount of the amide-based lubricant was the same as that in Example 7, but since the battery packaging materials were stored at a temperature of 40° C. and a temperature of 50° C., respectively, the intensity ratio X=P/Q decreased to a value lower than 0.05, leading to deterioration of moldability.

Examples 8 to 17 and Comparative Examples 7 to 15

<Production of Battery Packaging Material>

Both surfaces of an aluminum foil (thickness: 35 μm) as a metal layer were subjected to a chemical conversion treatment, and a biaxially stretched nylon film (thickness: 15 μm) was bonded to one of the chemical conversion-treated surfaces as a base material layer with a urethane resin-based adhesive interposed therebetween by a dry lamination method in such a manner that the thickness of an adhesive layer was about 3 μm. Next, an adhesive layer (carboxylic acid-modified polypropylene; thickness is as described in Table 1) with an amide-based lubricant (erucic acid amide) added thereto so as to achieve a content as described in Table 1, and a sealant layer (random copolymer of polypropylene; thickness is as described in Table 1) were melt-extruded to the other chemical conversion-treated surface to obtain a laminate including a base material layer, an adhesive agent layer, an aluminum foil, an adhesive layer and a sealant layer. Each packaging material was produced at a temperature of 25° C. The chemical conversion treatment was performed in the following manner: an aqueous solution including a phenol resin, a chromium fluoride compound and phosphoric acid was applied as a treatment liquid using a roll coating method, and baked under the condition of a film temperature of 180° C. or higher. The applied amount of chromium was 10 mg/m$^2$ (dry mass). The crystallinity degree of the sealant layer was adjusted by changing the cooling state during coextrusion and lamination of the adhesive layer and the sealant layer. Details of materials that form the base material layer, the adhesive agent layer, the metal layer, the adhesive layer and the sealant layer are as described below. The configurations of the obtained battery packaging materials are shown in Table 2.

<Base Material Layer>

Nylon: An unstretched raw film formed of a raw material mainly composed of nylon 6 was simultaneously biaxially stretched by a tubular method, and then heat-treated at 200° C. to produce a nylon film. The nylon film was produced under the condition of a draw ratio of 3.0 in the machine direction (MD) and 3.3 in the traverse direction (TD).

PET: An unstretched raw film formed of a raw material mainly composed of polyethylene terephthalate was sequentially biaxially stretched by a tenter method, and then heat-treated at 210° C. to produce a PET film. The PET film was produced under the condition of a draw ratio of 3.2 in the machine direction (MD) and 3.2 in the traverse direction (TD).

PBT: An unstretched raw film formed of a raw material mainly composed of polybutylene terephthalate was sequentially biaxially stretched by a tenter method, and then heat-treated at 205° C. to produce a PBT film. The PBT film was produced under the condition of a draw ratio of 3.8 in the machine direction (MD) and 3.8 in the traverse direction (TD).

<Adhesive Agent Layer>

A polyester resin-based adhesive obtained by mixing in a ratio of 1:3 a polyester polyol compound having a glass transition point of −5 to 5° C., a weight average molecular weight of $10 \times 10^3$ to $40 \times 10^3$ and a hydroxyl group equivalent of 0.7 to 1.9/mol and an aromatic isocyanate mainly composed of a trimethylolpropane (TMP) adduct of toluene diisocyanate (TDI) was used.

<Metal Layer>

An aluminum foil 8079 material having the properties shown below was used. Tensile rupture strength: MD 86.1 MPa, TD 85.7 MPa; Tensile rupture elongation: MD 12.5%, TD 11.6%; 0.2% yield strength: MD 38.2 MPa, TD 38.3 MPa.

The tensile rupture strength and the tensile rupture elongation are each a value measured by a method conforming to JIS K7127. The 0.2% yield strength is a value measured by a tensile test defined in JIS Z 2241 (total elongation method).

As a stainless foil, SUS 304 (austenite-based stainless steel) was used.

[Adhesive Layer]

For the adhesive layers in Examples 1 to 3 and 5 to 17 and Comparative Examples 1 to 15, random type polypropylene-based unsaturated carboxylic acid-modified polypropylene having a Vicat softening point of 105° C. and a melting point of 146° C. was used. For the adhesive layer in Example 4, unsaturated carboxylic acid-graft-modified random polyethylene graft-modified with an unsaturated carboxylic acid, which had a Vicat softening point of 107° C. and a melting point of 143° C., was used.

<Sealant Layer>

For the sealant layers in Examples 1 to 3 and 5 to 17 and Comparative Examples 1 to 15, random polypropylene having a melting point of 142° C., a melt index of 10 g/min and an ethylene content of 7% was used. For the sealant layer in Example 4, high-density polyethylene having a melting point of 125° C. and a melt index of 11 g/min was used.

For the battery packaging materials obtained in Examples 8 to 17 and Comparative Examples 7 to 15, evaluation of moldability, measurement of lamination strength, evaluation of continuous productivity of batteries, measurement of the crystallinity degree and infrared absorption spectrum measurement were performed in accordance with the following methods. The battery packaging materials of examples and comparative examples were left standing at a temperature of 25° C. and a relative humidity of 50% for 7 days, followed by performing these evaluations and measurements. The results thereof are shown in Table 3.

(Evaluation of Moldability)

Each of the battery packaging materials obtained in Examples 8 to 17 and Comparative Examples 7 to 15 was cut to a rectangle of 80 mm×120 mm to prepare a sample. Using a mold (female mold) having an opening size (rectangle) of 30 mm×50 mm and a corresponding mold (male mold), the obtained sample was cold-molded while the molding depth was changed by units of 0.5 mm from the molding depth of 0.5 mm under a pressing force of 0.4 MPa. This procedure was carried out for 10 samples at each depth. For the sample after the cold molding, the deepest of depths at which none of the 10 samples had creases, and pinholes and cracks in the aluminum foil was defined as the limit molding depth of the sample. From the limit depth, the moldability of the battery packaging material was evaluated in accordance with the following criteria.

A: the limit molding depth is 6.0 mm or more.
B: the limit molding depth is 4.0 mm to 5.5 mm.
C: the limit molding depth is 3.5 mm or less.

[Measurement of Lamination Strength Between Metal Layer and Adhesive Layer]

A sample having a width of 15 mm was cut out in a strip form from each of the battery packaging materials obtained in Examples 8 to 17 and Comparative Examples 7 to 15, and delaminated at the interface between the metal layer and the adhesive layer to prepare a measurement sample. Using the obtained measurement sample, lamination strength (peeling strength) between the metal layer and the adhesive layer was measured at a tension speed of 50 mm/min by a tension testing machine.

(Evaluation of Continuous Productivity)

For the sample after the "evaluation of moldability" performed as described above, a portion corresponding to the corner portion of the mold was visually observed. A sample was rated as having low continuous productivity (C) when the mold was whitened with the lubricant transferred thereto, and a sample was rated as having high continuous productivity (A) when the mold was not whitened.

(Crystallinity Degree)

The battery packaging material obtained in each of Examples 8 to 17 and Comparative Examples 7 to 15 was cut to a square of 50 mm×50 mm to prepare a sample, and for the surface of the sealant layer of the sample, a Raman optical spectrum was measured under the condition of a laser wavelength of 633 nm and a measurement time of 15 seconds using a microscopic laser Raman spectroscopic analyzer: LabRAM HR-800 (manufactured by HORIBA, Ltd./Jobin Yvon). A crystallinity degree was calculated from a peak at 809 cm$^{-1}$ originating from the crystalline portion of a resin for forming the sealant layer and a peak at 842 cm$^{-1}$ originating from the noncrystalline portion of the resin using the obtained spectrum.

(Infrared Absorption Spectrum Measurement in Infrared Spectroscopy)

Each of the battery packaging materials obtained in Examples 8 to 17 and Comparative Examples 7 to 15 was cut to a square of 100 mm×100 mm to prepare a sample. The surface of the heat-bondable resin layer of the obtained sample was subjected to infrared absorption spectrum measurement under an environment at a temperature of 25° C. and a relative humidity of 50% using the ATR measurement mode of Nicolet iS10 FT-IR manufactured by Thermo Fisher Scientific, Inc. A peak intensity P at 1650 cm$^{-1}$ originating from C=O stretching vibration of the amide group and a peak intensity Q at 1460 cm$^{-1}$ originating from bending vibration of the group —$CH_2$— of a polyolefin resin were each measured from the obtained absorption spectrum, and an intensity ratio X=P/Q of the peak intensity P to the peak intensity Q was calculated.

TABLE 2

|   | Base material layer [μm] | Metal Layer [μm] | Adhesive layer [μm] C | Sealant layer [μm] D | Concentration of lubricant in adhesive layer [ppm] A | Concentration of lubricant in sealant layer [ppm] B | Calculation formula Y | Total thickness of laminate [μm] |
|---|---|---|---|---|---|---|---|---|
| Example 8 | 15 | 35 | 10 | 10 | 10 | 1000 | 505 | 73 |
| Example 9 |  |  | 10 | 30 | 100 | 500 | 400 | 93 |
| Example 10 |  |  | 15 | 10 | 30 | 1800 | 738 | 78 |
| Example 11 |  |  | 20 | 20 | 10 | 1200 | 605 | 93 |
| Example 12 |  |  | 20 | 40 | 50 | 1000 | 683 | 113 |
| Example 13 |  |  | 25 | 15 | 80 | 800 | 350 | 93 |
| Example 14 |  |  | 30 | 10 | 1 | 2000 | 501 | 93 |
| Example 15 |  |  | 40 | 40 | 1 | 600 | 301 | 133 |
| Example 16 |  |  | 30 | 15 | 5 | 1500 | 503 | 98 |
| Example 17 |  |  | 30 | 15 | 5 | 1500 | 503 | 98 |
| Comparative Example 7 | 15 | 35 | 5 | 30 | 0 | 1000 | 857 | 88 |
| Comparative Example 8 |  |  | 10 | 10 | 20 | 3000 | 1505 | 73 |
| Comparative Example 9 |  |  | 10 | 30 | 50 | 300 | 238 | 93 |
| Comparative Example 10 |  |  | 20 | 20 | 200 | 100 | 150 | 93 |
| Comparative Example 11 |  |  | 25 | 15 | 800 | 500 | 688 | 93 |
| Comparative Example 12 |  |  | 30 | 10 | 50 | 500 | 163 | 93 |
| Comparative Example 13 |  |  | 40 | 40 | 1000 | 1500 | 1250 | 133 |
| Comparative Example 14 |  |  | 20 | 20 | 200 | 100 | 150 | 93 |
| Comparative Example 15 |  |  | 20 | 20 | 200 | 100 | 150 | 93 |

TABLE 3

|   | Lamination Strength between Metal Layer and Adhesive layer [N/15 mm] | Moldability | Continuous productivity | Crystallinity degree [%] | Intensity ratio X | Calculation formula Y |
|---|---|---|---|---|---|---|
| Example 8 | 6.5 | A | A | 38 | 0.38 | 505 |
| Example 9 | 7.0 | A | A | 48 | 0.15 | 400 |
| Example 10 | 7.5 | A | A | 38 | 0.69 | 738 |
| Example 11 | 8.7 | A | A | 43 | 0.45 | 605 |
| Example 12 | 8.3 | A | A | 49 | 0.41 | 683 |

TABLE 3-continued

|  | Lamination Strength between Metal Layer and Adhesive layer [N/15 mm] | Moldability | Continuous productivity | Crystallinity degree [%] | Intensity ratio X | Calculation formula Y |
|---|---|---|---|---|---|---|
| Example 13 | 9.1 | A | A | 43 | 0.16 | 350 |
| Example 14 | 10.9 | A | A | 35 | 0.80 | 501 |
| Example 15 | 12.5 | A | A | 52 | 0.18 | 301 |
| Example 16 | 11.0 | A | A | 43 | 0.61 | 503 |
| Example 17 | 11.2 | A | A | 27 | 0.53 | 503 |
| Comparative Example 7 | 5.5 | A | C | 62 | 0.82 | 857 |
| Comparative Example 8 | 6.8 | A | C | 38 | 1.27 | 1505 |
| Comparative Example 9 | 6.8 | C | A | 49 | 0.03 | 238 |
| Comparative Example 10 | 5.2 | C | A | 43 | 0.01 | 150 |
| Comparative Example 11 | 4.1 | B | A | 48 | 0.14 | 688 |
| Comparative Example 12 | 10.8 | B | A | 40 | 0.04 | 163 |
| Comparative Example 13 | 5.9 | A | C | 64 | 0.92 | 1250 |
| Comparative Example 14 | 4.7 | C | A | 66 | 0.04 | 150 |
| Comparative Example 15 | 5.3 | C | A | 15 | 0.00 | 150 |

As shown in Table 2 and Table 3, the battery packaging material of Examples 8 to 17 where the amount of the lubricant contained in the adhesive layer is 100 ppm or less, and the value Y calculated from the calculation formula (1) is in the range of 250 to 750 have excellent moldability and high lamination strength between the metal layer and the adhesive layer, and are excellent in continuous productivity of batteries.

For example, comparison between Example 12 and Comparative Example 7 with the same amount (1000 ppm) of the lubricant added to the sealant layer shows that in Example 12 and Comparative Example 7, the amount of the lubricant in each of the adhesive layer and the sealant layer and the thickness of each of these layers are each set to a desired value as an independent value. However, in Comparative Example 7 with the value Y falling out of the range of 250 to 750, the battery packaging material was excellent in moldability, but was poor in continuous productivity of batteries, and had a low value of lamination strength between the metal layer and the adhesive layer. The reason for this may be as follows. That is, it is considered that in the battery packaging material of Comparative Example 7, the adhesive layer had a small thickness of 5 μm, and therefore, the concentration of the lubricant in the adhesive layer increased at the time when the lubricant contained in the sealant layer was transferred to the adhesive layer. It is considered that accordingly, lamination strength between the metal layer and the adhesive layer decreased. It is considered that on the other hand, the sealant layer contained a large amount of the lubricant, and therefore the battery packaging material was excellent is moldability, but an excessively large amount of the lubricant was bled out, so that continuous productivity of batteries was deteriorated.

For example, comparison between Example 9 and Comparative Example 12 with the same amount (500 ppm) of the lubricant blended in the sealant layer shows that in Example 9 and Comparative Example 12, the amount of the lubricant in each of the adhesive layer and the sealant layer and the thickness of each of these layers are each set to a desired value as an independent value. However, in Comparative Example 12, the battery packaging material had high lamination strength between the metal layer and the adhesive layer, but was poor in moldability. The reason for this may be as follows. In the battery packaging material of Comparative Example 12, the adhesive layer has a large thickness of 30 μm. The amount of the lubricant added to the sealant layer is 500 ppm, and the amount of the lubricant added to the adhesive layer is 50 ppm. Either of these values is not high. It is considered that accordingly, the lubricant contained in the sealant layer was transferred in a large amount to the adhesive layer, so that the amount of the lubricant in the sealant layer decreased, and thus the adhesive layer had a desired amount of the lubricant. It is considered that accordingly, moldability was deteriorated, and lamination strength between the metal layer and the adhesive layer did not decrease.

DESCRIPTION OF REFERENCE SIGNS

1: Base material layer
2: Adhesive agent layer
3: Metal Layer
4: Sealant layer
5: Adhesive layer

The invention claimed is:

1. A battery packaging material comprising a laminate in which at least a base material layer, a metal layer, an adhesive layer, and a sealant layer containing a polyolefin resin are laminated in this order, wherein
the sealant layer contains an amide-based lubricant,
an amount of the amide-based lubricant in the adhesive layer is 100 ppm or less,
the value Y calculated from the following formula (1) is in the range of 250 to 750:

$$Y=(A\times C+B\times D)/(C+D) \tag{1}$$

where:
A represents an amount of the amide-based lubricant in the sealant layer, B represents an amount of the amide-based lubricant in the adhesive layer, C represents a thickness of the sealant layer, and D represents a thickness of the adhesive layer, and the intensity ratio X=P/Q is in a range of from 0.05 to 0.80, where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

2. The battery packaging material according to claim 1, wherein the amide-based lubricant is at least one of a fatty acid amide and an aromatic bis-amide.

3. The battery packaging material according to claim 1, wherein an adhesive agent layer is laminated between the base material layer and the metal layer.

4. The battery packaging material according to claim 1, wherein the amount of the amide-based lubricant to the sealant layer is 500 to 2000 ppm.

5. The battery packaging material according to claim 1, wherein the sealant layer has a thickness of 10 to 30 μm.

6. The battery packaging material according to claim 1, wherein the adhesive layer has a thickness of 10 to 30 μm.

7. The battery packaging material according to claim 1, wherein the laminate has a thickness of 120 μm or less.

8. The battery packaging material according to claim 1, wherein the sealant layer has a crystallinity degree of 30 to 60% as calculated from the spectral intensity ratio of a crystalline portion and a noncrystalline portion of the sealant layer using a Raman spectroscopic method.

9. The battery packaging material according to claim 1, wherein the metal layer is formed of an aluminum foil.

10. A method for producing a battery packaging material, the method comprising:

providing a battery packaging material including a laminate in which at least a base material layer, a metal layer, and a sealant layer containing a polyolefin resin are laminated in this order; and molding the battery packaging material when an intensity ratio X=P/Q is in a range of from 0.05 to 0.80, where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q.

11. A battery comprising a battery element which includes at least a positive electrode, a negative electrode and an electrolyte, the battery element being stored in the battery packaging material according to claim 1.

12. A method for producing a battery, the method comprising:

providing a battery packaging material including a laminate in which at least a base material layer, a metal layer, and a sealant layer containing a polyolefin resin are laminated in this order, the battery packaging material having an intensity ratio X=P/Q in a range of from 0.05 to 0.80, where P is a peak intensity P at 1650 cm$^{-1}$ originating from C=O stretching vibration of the amide group of an amide-based lubricant, and Q is a peak intensity Q at 1460 cm$^{-1}$ originating from bending vibration of the group —CH$_2$— of the polyolefin resin, each of which is measured from an absorption spectrum obtained by splitting reflected light in irradiation of the surface of the sealant layer with an infrared ray, and P/Q is a ratio of the peak intensity P to the peak intensity Q; and molding the battery packaging material, and storing in the battery packaging material a battery element including at least a positive electrode, a negative electrode, and an electrolyte.

* * * * *